US012735667B2

(12) United States Patent
Tachino et al.

(10) Patent No.: US 12,735,667 B2
(45) Date of Patent: Sep. 15, 2026

(54) CELL CULTURE SUBSTRATE AND CELL CULTURE SCAFFOLD KIT

(71) Applicant: Sharp Display Technology Corporation, Kameyama City (JP)

(72) Inventors: Chihiro Tachino, Kameyama City (JP); Takeshi Hara, Kameyama City (JP); Tomoko Teranishi, Kameyama City (JP); Satoshi Ihida, Kameyama City (JP)

(73) Assignee: Sharp Display Technology Corporation, Kameyama City (JP)

( * ) Notice: Subject to any disclaimer, the term of this patent is extended or adjusted under 35 U.S.C. 154(b) by 782 days.

(21) Appl. No.: 18/123,209

(22) Filed: Mar. 17, 2023

(65) Prior Publication Data

US 2023/0323266 A1 Oct. 12, 2023

(30) Foreign Application Priority Data

Mar. 23, 2022 (JP) ................................ 2022-046327

(51) Int. Cl.
*C12M 1/12* (2006.01)
*C12N 5/00* (2006.01)

(52) U.S. Cl.
CPC ........... *C12M 25/14* (2013.01); *C12N 5/0068* (2013.01)

(58) Field of Classification Search
CPC ............................ C12N 5/0068; C12M 25/14
USPC ...................................................... 435/305.1
See application file for complete search history.

(56) References Cited

U.S. PATENT DOCUMENTS

2004/0209352 A1* 10/2004 Ozaki .................... C12Q 1/001 435/287.1
2004/0235167 A1 11/2004 Miyake et al.
2024/0209352 A1* 6/2024 Doudna ............. C12N 15/1079

FOREIGN PATENT DOCUMENTS

JP 2005229914 A 9/2005
JP 4201182 B2 12/2008

* cited by examiner

*Primary Examiner* — Michael L Hobbs
*Assistant Examiner* — Lenora A Abel
(74) *Attorney, Agent, or Firm* — ScienBiziP, P.C.

(57) ABSTRACT

A cell culture substrate includes a base, a first segment disposed on the base and occupying a part of one surface of the cell culture substrate, and a second segment disposed on the base and occupying another part of the one surface. The second segment is formed of a metal material and thus has a relatively higher surface free energy than the first segment formed of an inorganic material. The second segment is disposed such that a percentage of an area of the second segment in a total area of the first segment and the second segment increases in a gradation direction (first direction) along the one surface.

16 Claims, 10 Drawing Sheets

CELL CULTURE SUBSTRATE AND CELL CULTURE SCAFFOLD KIT

BACKGROUND

1. Field

The technology disclosed herein relates to a cell culture substrate and a cell culture scaffold kit.

2. Description of the Related Art

A micropatterned substrate is known that has a surface whose cell adhesiveness is controlled for the purpose of immobilizing and culturing living cells in an arrangement. For example, Japanese Patent No. 4201182 discloses a cell culture substrate including a cell adhesiveness-variable layer and a photocatalyst-containing layer. The cell adhesiveness-variable layer contains a biological cell adhesiveness-variable material such as a cell-adhesive protein, and the photocatalyst-containing layer contains a photocatalyst and a biological cell adhesiveness-variable material whose cell adhesiveness has been changed by photocatalytic action. The cell adhesiveness-variable layer and the photocatalyst-containing layer are formed in a pattern. Japanese Unexamined Patent Application Publication No. 2005-229914 discloses a microstructure for cell culture including a cell adhesion portion and a cell adhesion-assisting portion. The cell adhesion portion includes a cell-adhesive layer having adhesiveness to cells, and the cell adhesion-assisting portion is formed in a pattern and inhibits adhesion to cells.

SUMMARY

In the cell culture substrate and the microstructure for cell culture disclosed in Japanese Patent No. 4201182 and Japanese Unexamined Patent Application Publication No. 2005-229914, cells preferentially grow on highly cell-adhesive surfaces including cell-adhesive proteins and the like serving as scaffolds, and thus the direction of cell growth can be controlled. However, such a cell culture substrate preliminarily provided with a biological cell adhesiveness-variable material is stored under strict conditions because of the instability of a cell-adhesive protein and can hardly maintain its quality in an unused state.

It is desirable to provide a cell culture substrate that allows a culture scaffold having a controlled cell culture environment to be prepared at any timing and to provide a cell culture scaffold kit.

According to an aspect of the disclosure, there is provided a cell culture substrate used to prepare a cell culture scaffold. The cell culture substrate includes a base, a first segment disposed on the base and occupying a part of one surface of the cell culture substrate, and a second segment disposed on the base and occupying another part of the one surface. The second segment has a relatively higher surface free energy than the first segment and is disposed such that a percentage of an area of the second segment in a total area of the first segment and the second segment increases in a first direction that is a direction along the one surface.

According to another aspect of the disclosure, there is provided a cell culture scaffold kit including the cell culture substrate and a reagent containing a coating agent for forming a medium disposed on the cell culture substrate.

DESCRIPTION OF THE EMBODIMENTS

Hereinafter, some embodiments of the technology disclosed herein will be described. Matters (e.g., general matters regarding a cell to be cultured, a technology for culturing the cell, and screening and preparation of a pharmaceutical composition, and general matters regarding micromachining technology related to the manufacture of a cell culture substrate) that are other than matters particularly mentioned in the present specification (e.g., a structure of a cell culture substrate disclosed herein) and that are necessary for carrying out the present technology can be understood to be matters of design variation made by those skilled in the art on the basis of the related art in the fields of cytology, physiology, medicine, pharmacy, biochemistry, genetic engineering, protein engineering, material engineering, semiconductor engineering, ultra-precision machining technology, MEMS engineering, and the like. The present technology can be carried out on the basis of the contents of the present specification and general technical knowledge in the related fields.

Cell Culture Substrate

A cell culture substrate according to an embodiment will be described with reference to FIGS. 1 to 6 as appropriate. In some figures, an X axis, a Y axis, and a Z axis are illustrated so as to extend respectively along a gradation direction (an example of a first direction), a cross direction, and a thickness direction in the present technology. The side toward which the Z axis extends is a cell culture surface side, and the opposite side is a back surface side.

A cell culture substrate 1 is a substrate for creating thereon a culture environment (e.g., a medium) for culturing various cells. The cell culture substrate 1 according to this embodiment further has a function to record an electrical signal (action potential) emitted by a cultured cell in a non-invasive manner outside the cell. Among living cells, normal cells other than hematopoietic cells cannot grow or divide in a floating state and need to adhere to other cells or matrices serving as scaffolds. In addition, cell culture substrates have low affinity for cells. Thus, when a cell is cultured, a surface 1A of the cell culture substrate 1 is typically treated with an extracellular matrix (ECM) which has high affinity for the cell and improves adhesion of the cell. On the cell culture substrate 1 according to the present technology, a medium containing a preference component such as an extracellular matrix to which the cell exhibits preference can be formed such that the preference component is distributed with a concentration gradient. As a result, in a culture region C where the preference component is distributed at a concentration preferred by the cell to be cultured, the cell can be selectively grown. If the culture region C is anisotropically formed, the cell can be grown along a predetermined direction.

Figure 1:
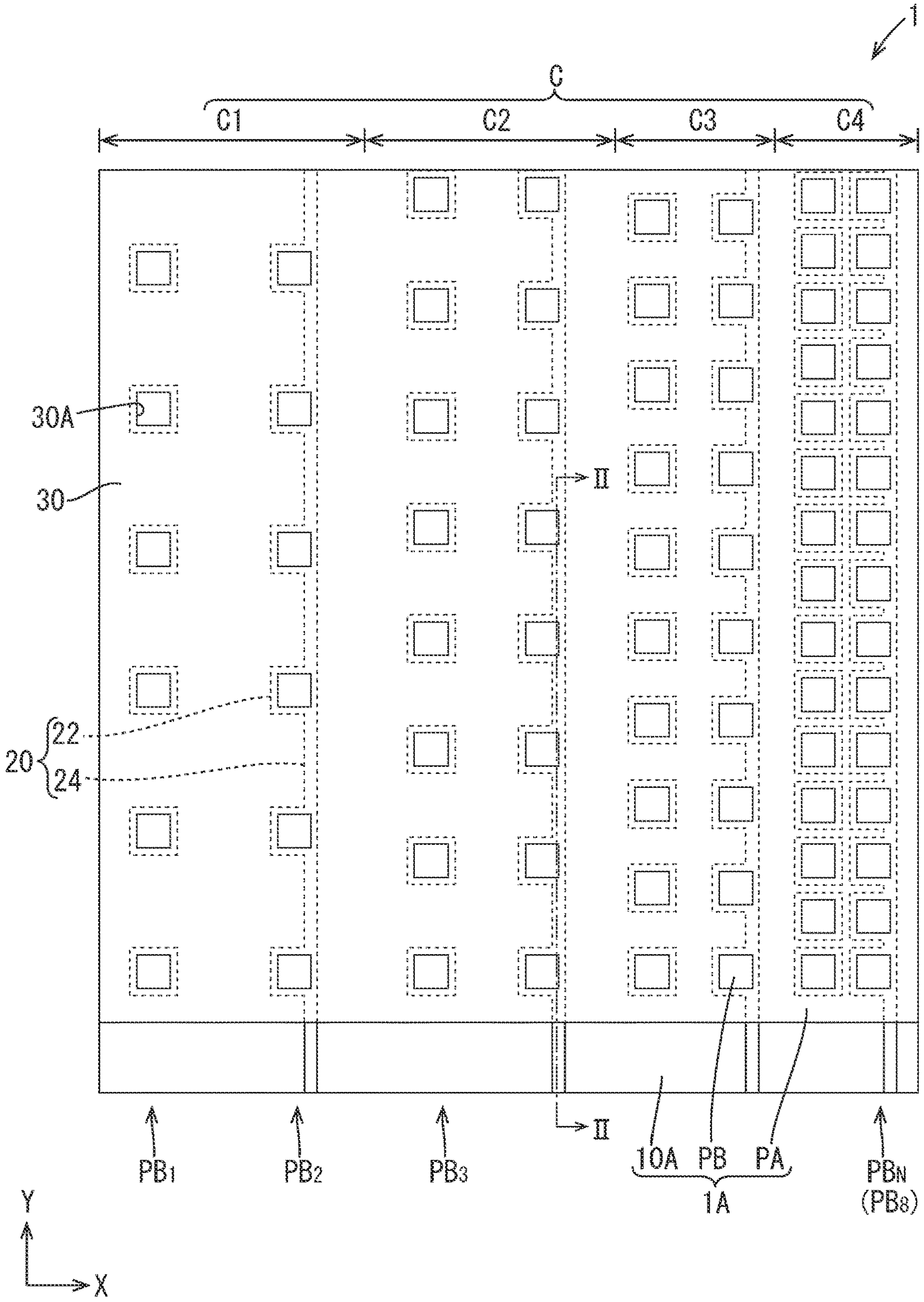
FIG. 1 is a plan view schematically showing the principal part of a cell culture substrate according to a first embodiment.
Figure 2:
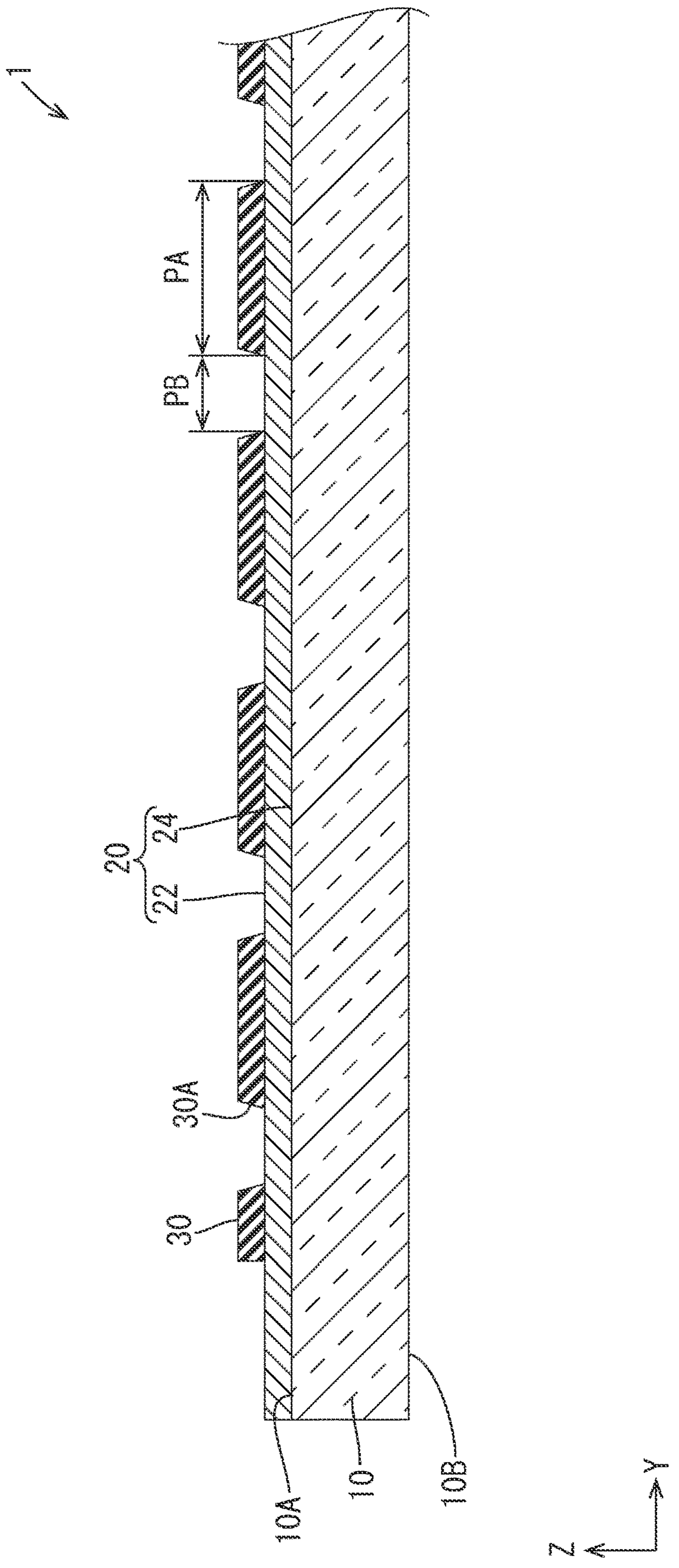
FIG. 2 is a sectional view of the cell culture substrate in FIG. 1 taken along II-II.

As shown in FIGS. 1 and 2, the cell culture substrate 1 includes a base 10, a conductive layer 20, and an insulating layer 30. The surface 1A of the cell culture substrate 1 on the side on which a cell is cultured includes a first segment PA of the present technology and a second segment PB of the present technology. The surface 1A may include an exposed portion of a main surface 10A of the base 10 described later.

First, the properties of the surface 1A of the cell culture substrate 1 will be described. The first segment PA is a segment having a relatively low surface free energy. The second segment PB is a segment that has a relatively higher surface free energy than the first segment PA. The second segment PB, because of having a surface free energy relatively higher than that of the first segment PA, has relatively high hydrophilicity. The first segment PA, because of having a surface free energy relatively lower than that of the second segment PB, has relatively high water repellency. The surface free energy (a value at 20° C., hereinafter the same shall apply) of the first segment PA is typically less than 100 dyn/cm and may be, for example, 50 dyn/cm or less, although these values are not limitative. The surface free energy of the second segment PB may be any value higher than that of the first segment PA, but it is typically 100 dyn/cm or more and may be, for example, 200 dyn/cm or more. With this configuration, an aqueous solution is more likely to remain in the second segment PB than in the first segment PA on the surface 1A of the cell culture substrate 1. In other words, a coating solution for forming a coating layer containing a preference component such as an extracellular matrix is more readily supplied to the second segment PB than to the first segment PA.

In the surface 1A in this embodiment, a plurality of second segments PB are arranged in the first segment PA. The plurality of second segments PB are each surrounded by the first segment PA, and the first segment PA extends between the plurality of second segments PB. The plurality of second segments PB are disposed such that a percentage R of an area $S_2$ of the second segments PB in a total area $S_{12}$ of the first segment PA and the second segments PB (where $R\ (\%)=S_2 \div S_{12} \times 100$) increases in a predetermined gradation direction (X axis direction). The gradation direction is a direction along the surface 1A. The gradation direction refers to a direction in which the percentage R of the area $S_2$ of the second segments PB changes stepwise in terms of the size, number, etc. of the second segments PB in this embodiment. However, the percentage R of the area $S_2$ of the second segments PB may change continuously in the first direction in the present technology.

More specifically, the plurality of second segments PB is divided into N (N is a natural number) subgroups of a first group $PB_1$, a second group $PB_2$, . . . an N-th group $PB_N$. In this embodiment, N=8 is employed for convenience, although this value is not limitative. The second segments PB belonging to each subgroup are arranged along a cross direction (Y axis direction) intersecting the gradation direction. The subgroups are arranged in order from the first group $PB_1$ to the N-th group $PB_N$ so as to be spaced from each other in the gradation direction. Here, the number of second segments PB belonging to each subgroup remains the same or increases from the first group $PB_1$ to the N-th group $PB_N$. The interval between adjacent arrays of subgroups remains the same or decreases from the first group $PB_1$ to the N-th group $PB_N$. In this configuration, the number density of the second segments PB increases in the gradation direction. For example, when the plurality of second segments PB are identical and the surface 1A of the cell culture substrate 1 is divided into a plurality of regions extending in the cross direction, the percentage R of the area $S_2$ of the second segments PB in each region increases in the gradation direction. In an example specifically shown in FIG. 1, when the surface 1A of the cell culture substrate 1 is sequentially divided in the gradation direction into four culture regions C1 to C4 extending in the cross direction, percentages $R_2$, $R_3$, and $R_4$ of the second segments PB in the culture region C2, C3, and C4 increase in order with respect to a percentage $R_1$ of the second segments PB in the culture region C1. As a result, the hydrophilicity in the culture regions C1, C2, C3, and C4 increases in the gradation direction.

Hereinafter, a configuration of the cell culture substrate 1 including the first segment PA and the second segment PB as described above will be described.

Base

The base 10 is an element that supports the conductive layer 20 and the insulating layer 30 described above. The base 10 can also be a stage for supporting a medium for a cell to be cultured and observed and seeding and culturing the cell. The base 10 in this embodiment has a flat shape. The base 10 has the main surface 10A and a back surface 10B opposite to the main surface 10A. The main surface 10A is a surface on the side on which a cell is cultured and has the conductive layer 20 and the insulating layer 30 disposed thereon.

The base 10 is formed of an insulating material having electrical insulating properties. The insulating material is, for example, a material having a volume resistivity of $10^7$ Ωcm or more (e.g., $10^{10}$ Ωcm or more, $10^{12}$ Ωcm or more, or $10^{15}$ Ωcm or more) at room temperature (e.g., 25° C.), and may be, for example, an organic material or inorganic material having such a volume resistivity. The base 10 may be, but not necessarily, formed of a transparent material so that cells can be observed through the base 10 from the back surface side. The base 10 may be, for example, colorless and transparent.

Examples of materials forming the base 10 include various types of glass and synthetic resins. Suitable examples of glass include soda-lime glass, borosilicate glass, and quartz glass. The glass typically has a relatively low surface free energy of 100 dyn/cm or more, for example, about 200 to 300 dyn/cm, and can be considered as a constituent material of the first segment PA. The glass may be, but not necessarily, alkali-free glass, in which the content of alkali components in terms of oxides is 0.1 mass % or less and elution of alkali ions is suppressed. Examples of synthetic resins include synthetic resins such as polystyrene, polydimethylsiloxane (PDMS), polypropylene, polyethylene terephthalate (PET), polymethyl methacrylate (acrylic resin), polyimide, nylon, and polyurethane, each having a relatively high volume resistivity (e.g., $\mathbf{10}^{10}$ Ωcm or more, $10^{12}$ Ωcm or more, or $10^{15}$ Ωcm or more) and biocompatibility. The thickness of the base 10 may be, for example, about 0.1 to 2 mm (e.g., 0.5 mm, 0.7 mm, or 1 mm), although these values are not limitative.

Conductive Layer

The second segment PB in this embodiment is constituted by the conductive layer 20. The conductive layer 20 is formed of a material having electrical conductivity. The conductive layer 20 in this embodiment is also an element for detecting an action potential emitted by a cell. Details of the material forming the conductive layer 20 will be described later. The conductive layer 20 is disposed in layer form on the base 10. The conductive layer 20 in this embodiment includes an electrode portion 22 and a wiring portion 24. The conductive layer 20 may be typically, but not necessarily, disposed on the base 10 in a direct manner (i.e., without any intermediate layer).

The electrode portion 22 is an element that constitutes the second segment PB by not being covered by the insulating layer 30, which will be described later. The electrode portion 22 is typically formed larger than the second segment PB. The electrode portion 22 is an element that receives an action potential (electrical signal) emitted by a cell. The wiring portion 24 is a wire for sending the action potential received by the electrode portion 22 to a position of connection with a potential meter (not shown). The wiring portion 24, which is linear, is connected to one or more electrode portions 22 and also extends to an end portion of the base 10. An end portion of the wiring portion 24 that is disposed on the end portion of the base may be formed as a connection terminal wider than other portions in order to ensure the connection with the potential meter. Portions of the wiring portion 24 other than the end portion are covered by the insulating layer 30, which will be described later. In this embodiment, the wiring portion 24 extends in the cross direction, but the wiring portion 24 may extend in the gradation direction. One wiring portion 24 is disposed in each of the culture regions C1, C2, C3, and C4, that is, a plurality of wiring portions 24 are disposed as a whole (a plurality of wiring portions 24 may be disposed in each region), although this configuration is not limitative. All of the electrode portions 22 may be connected to the wiring portion 24, or some of the electrode portions 22 may be unconnected to the wiring portion 24.

The conductive material forming the conductive layer 20 may be, for example, a metal material, a conductive resin material, or a conductive inorganic material as long as an appropriate surface free energy relationship is satisfied between the conductive layer 20 and the insulating layer 30. From the viewpoint of high thermal stability and high electrical conductivity, a metal material may be used. The metal material may be used also because it can have a surface free energy of typically several hundred dyn/cm or more, for example, as high as 400 to 1500 dyn/cm. The metal material may be, for example, any one metal selected from metals such as gold (Au), silver (Ag), copper (Cu), titanium (Ti), aluminum (Al), nickel (Ni), chromium (Cr), molybdenum (Mo), niobium (Nb), tantalum (Ta), and tungsten (W), an alloy containing the metal, or an alloy containing any two or more metals selected from these metals. Metals containing these elements can reduce resistivity even when fine electrodes and wires are formed at points with high electrical conductivity. Suitable examples of metal materials include Au, W, Ti, Al, TaN (tantalum nitride), MoW (molybdenum tungsten alloy), and TiN (titanium nitride). When the conductive layer 20 has a multilayer structure, layers disposed closer to the base 10 and a layer in contact with the base 10 may be formed of metals with relatively high melting points, such as Ta, W, Mo, Ni, and Ti. For example, from the viewpoint of avoiding signal degradation, layers disposed at positions relatively far from the base 10 may be formed of metals with relatively low resistance, such as Au, Al, and Cr. To reduce wiring resistance, for example, a single-layer structure composed of a low-resistance MoW alloy may be employed, or a multilayer structure of, for example, W/TaN, Ti/Al/Ti, or Cu/Ti in order from the upper layer side may be employed so as to achieve both adhesion to a substructure (e.g., a base) and low resistance. Suitable examples of metal materials forming a conductive layer disposed at a position where it can be in contact with cells include Au, Ti, and TiN (titanium nitride), which have low cytotoxicity. The conductive layer 20 in this embodiment is formed of any of these metal materials.

Suitable examples of conductive resin materials include conductive polyacetylene, conductive polythiophene, conductive polyaniline, and conductive polyethylenedioxythiophene (PEDOT). Suitable examples of conductive inorganic materials include tin oxide ($SnO_2$; including tin oxide with Sb (antimony), Ta, F (fluorine), or the like added), zinc oxide (ZnO; including zinc oxide with Al, Ga (gallium), or the like added), and semiconductor oxides (which may be metal oxides) having a band gap of 3 eV or more, such as indium tin oxide (ITO), indium zinc oxide (IZO), and indium gallium zinc oxide (IGZO). These semiconductor oxides are also suitable in that they are transparent and have confirmed to be biologically bioinert. The electrode portion 22 may be formed wider than the wiring portion 24. In this case, the electrode portion 22 may be formed of a material transparent to visible light similarly to the base 10 because when a cell S to be cultured is observed through the back surface 10B of the base 10, the cell S is not hidden by the electrode portion 22. For example, the electrode portion 22 in this embodiment is formed of ITO. By employing such a material, the conductive layer 20 can be stable and less cytotoxic.

When the electrode portion 22 of the conductive layer 20 is formed of a conductive resin material or a conductive inorganic material, the surface free energy of the second segment PB constituted by the electrode portion 22 may probably be not so high. Therefore, at least a part of the conductive layer 20 that constitutes the second segment PB may be subjected to at least one of a surface treatment for increasing the surface free energy and a surface treatment for increasing hydrophilicity.

As such a surface treatment, various known methods for improving hydrophilicity such as corona discharge treatment and plasma treatment can be employed. Examples include plasma treatment by irradiation with air plasma, oxygen plasma, argon plasma, or the like, and corona discharge treatment and plasma treatment to introduce highly hydrophilic functional groups such as hydroxy, carboxy, and carbonyl groups. The surface subjected to such a treatment typically has a contact angle with water of 90° or less, for example, 45° or less, 30° or less, 15° or less, or 10° or less. This configuration allows a coating solution to be supplied in a larger amount to the second segment PB than to the first segment PA, thus further increasing the gradient of density distribution of the second segment PB in the gradation direction. As a result, when a cell culture scaffold 50 is prepared, the gradient of concentration distribution of an extracellular matrix can be further increased, thus increasing the effect of adjusting the direction of cell growth to align with the cross direction.

Insulating Layer

The first segment PA in this embodiment is constituted by the insulating layer 30. The insulating layer 30 is formed of an insulating material. Details of the material forming the insulating layer 30 will be described later. The insulating layer 30 in this embodiment, at a position corresponding to the first segment PA, covers the main surface 10A of the base 10 with the conductive layer 20 interposed therebetween. Accordingly, the insulating layer 30 insulates at least the wiring portion 24 of the conductive layer 20 from a cell culture environment, for example, in the culture region C. The insulating layer 30 has an opening 30A at a position corresponding to the second segment PB. As a result, the electrode portion 22 of the conductive layer 20 is exposed at the surface 1A through the opening 30A of the insulating layer 30 to constitute the second segment PB. In addition, the insulating layer 30 has an opening 30A at a position corresponding to the second segment PB to expose the conductive layer 20 at the surface 1A through the opening 30A. At an edge of the base 10, that is, a region where the end portion of the wiring portion 24 is disposed, the insulating layer 30 may expose the main surface 10A at the surface 1A without covering the base 10.

The opening 30A of the insulating layer 30 is disposed so as to provide the arrangement of the plurality of second segments PB, as described above. The shape of the opening 30A, in other words, the shape of the second segment PB, is not particularly limited and may be, for example, polygonal, e.g., linear, rectangular, square, rhombic, or triangular, round, or irregular. The opening 30A (i.e., the second segment PB) in this embodiment has a square shape. The size of one opening 30A (i.e., one second segment PB) is not particularly limited. From the viewpoint of increasing the adhesion to cells, the diameter of the minimum circumscribed circle of one opening 30A (i.e., one second segment PB) may be about 1 μm or more and 1000 μm or less, for example, about 2 μm or more (2.5 μm or more) and 500 μm or less (100 μm or less). The second segment PB having such a size is suitable because when a cell culture scaffold is produced using the cell culture substrate 1, a density distribution of the second segment PB in the gradation direction is readily achieved that allows the concentration of an extracellular matrix to be easily adjusted to various concentration distributions that can accommodate preferences of various cells S.

The insulating layer 30 may be formed of the same material having electrical insulating properties as that of the base 10. The insulating layer 30 may be formed of a material that exhibits stable electric insulation in a cell culture environment. Considering that the insulating layer 30 is formed so as to be in contact with the base 10 and the conductive layer 20 and have the very small opening 30A, the insulating layer 30 may be formed of, for example, an inorganic material such as silicon nitride (e.g., $Si_3N_4$), silicon oxide (e.g., $SiO_2$), or silicon oxynitride (e.g., $Si_2N_2O$), although these materials are not limitative. To effectively achieve a low surface free energy, the insulating layer 30 may be formed of, for example, a resin having a surface free energy of about 50 dyn/cm or less, such as polyimide (about 50 dyn/cm), acrylic resin (about 40 dyn/cm), polyethylene (about 30 dyn/cm), or fluorocarbon resin (about 20 dyn/cm). The insulating layer 30 may have a single-layer structure composed of any one of these materials or a multilayer structure composed of any two or more of these materials. For the materials described above, representative compositions or representative surface free energies are shown in parentheses, but these compositions and surface free energies of the materials are not limitative.

When the insulating layer 30 is formed of an inorganic material, the surface free energy of the first segment PA may probably be not so lower than that of the second segment PB. Therefore, the insulating layer 30 may be subjected to at least one of a surface treatment for decreasing the surface free energy and a surface treatment for increasing water repellency.

Examples of such surface treatments include coating of the surface of the insulating layer 30 with a highly water-repellent material such as a fluorocarbon resin represented by polytetrafluoroethylene (PTFE) or a compound having a perfluoro group and formation of microscopic asperities of several μm to several nm on the surface of the insulating layer 30 by laser processing, transcription, or other method. The surface subjected to such a treatment may typically have a contact angle with water of more than 90°, for example, 110° or more, 130° or more, 140° or more, or 150° or more.

Manufacturing Method

Figures 4A, 4B, 4C, 4D, 4E, 4F:
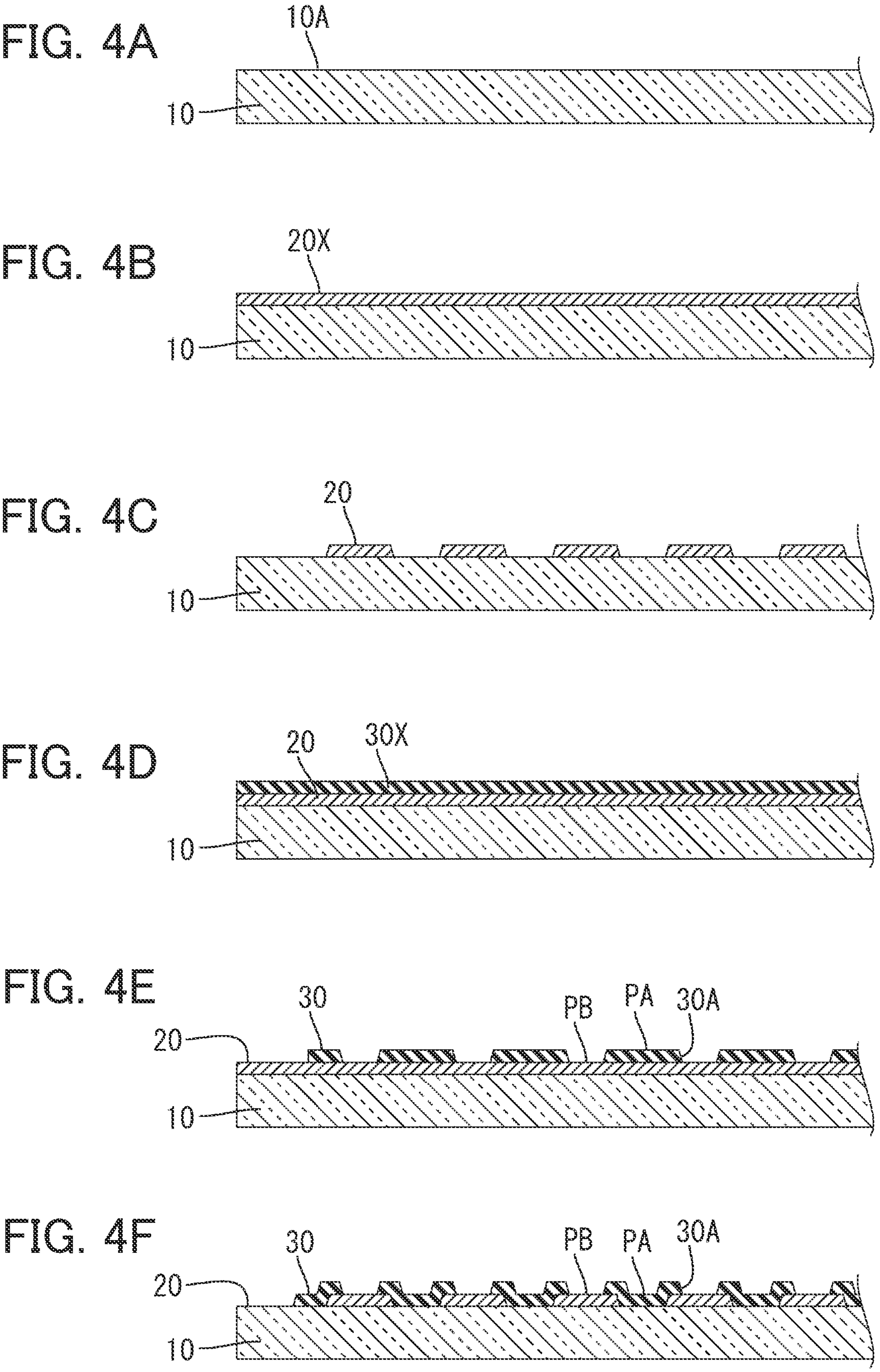
FIG. 4A is a sectional view showing a step in a method for manufacturing a cell culture substrate.
FIG. 4B is a sectional view showing another step in the method for manufacturing a cell culture substrate.
FIG. 4C is a sectional view showing another step in the method for manufacturing a cell culture substrate.
FIG. 4D is a sectional view showing another step in the method for manufacturing a cell culture substrate.
FIG. 4E is a sectional view showing another step in the method for manufacturing a cell culture substrate.
FIG. 4F is a sectional view showing another step in the method for manufacturing a cell culture substrate.
Figure 5:
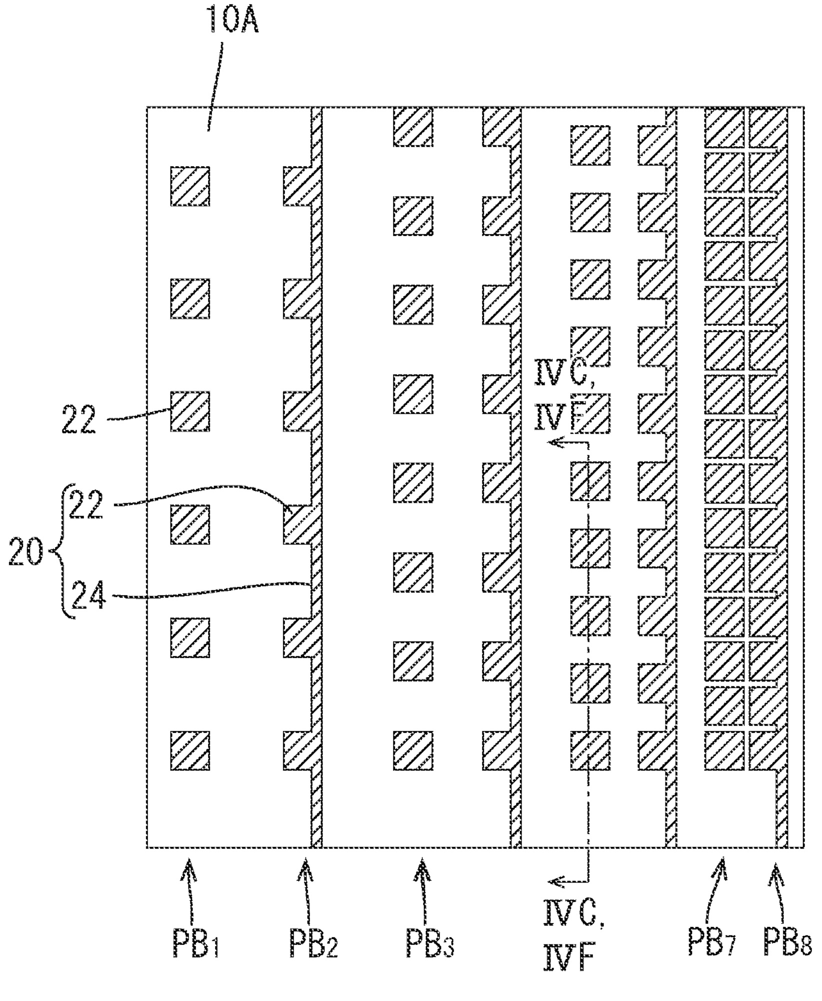
FIG. 5 is a plan view corresponding to FIG. 4C.

The method for manufacturing the cell culture substrate 1 described above is not particularly limited. The cell culture substrate 1 can be suitably produced by, for example, the following procedure according to an embodiment. Specifically, first, a base 10 formed of a colorless transparent alkali-free glass plate (0.7 mm thick) or the like is provided, as shown in FIG. 4A. Next, a conductive layer 20X is formed on a culture region C on a main surface 10A of the base 10 by a film formation process such as sputtering or vapor deposition, as shown in FIG. 4B. In this embodiment, the conductive layer 20X is formed using a conductive material such as gold or titanium which has low cytotoxicity and is patternable by photolithography. The conductive layer 20X may be used as it is (as having a solid surface), but in this embodiment, portions other than an electrode portion 22 and a wiring portion 24 are removed by lithography technology (e.g., photolithography or laser lithography) to form a pattern having a shape shown in FIGS. 4C and 5, for example. To reduce electrical resistance, the conductive layer 20X may have, for example, a single-layer structure composed of a low-resistance MoW alloy or a multilayer structure such as W/TaN or Ti/Al/Ti, or may be formed of transparent ITO or the like. The thickness of the conductive layer 20 is not particularly limited and may be, for example, about 50 nm or more and 1000 nm or less.

In the case of photolithography technology, typically, a resist solution is applied in a predetermined pattern shape to a film to be patterned (here, the conductive layer 20X), exposed, and rinsed to thereby form a photoresist pattern. Using the photoresist pattern as a mask, the conductive layer 20X is then etched. As a result, a portion of the conductive layer 20X that is not covered by the mask is removed, whereby a conductive layer 20 having a desired pattern shape can be obtained. When a wide connection terminal is provided at an end of the wiring portion 24, the connection terminal is formed at the time of the patterning. As a result, a conductive layer 20 having a predetermined shape is formed.

Next, the main surface 10A of the base 10 and the upper surface of the conductive layer 20 formed are covered with an insulating layer 30X, as shown in FIG. 4D. In this embodiment, a transparent insulating layer 30X is formed using an insulating inorganic material such as silicon nitride, silicon dioxide, or silicon oxynitride. The thickness of the insulating layer 30X is not particularly limited and may be, for example, about 300 nm or more and 900 nm or less. Thereafter, an opening 30A is formed on a part of the insulating layer 30X that overlaps with the electrode portion 22, as shown in FIGS. 4E and 4F. The opening 30A can be formed in the same manner as described above by removing the insulating layer 30X by etching or the like. A technique for forming a contact hole in the semiconductor microfabrication technology can be applied to the formation of the opening 30A. At this time, to facilitate electrical connection between the wiring portion 24 and an external device, a portion of the insulating layer 30X that is located at an end portion of the main surface 10A may also be removed to expose the end portions of the main surface 10A and the wiring portion 24. As a result, the insulating layer 30 constituting the first segment is formed, whereby the cell culture substrate 1 disclosed herein can be obtained.

Operation and Effect

The cell culture substrate 1 described above includes a base 10, a first segment PA disposed on the base 10 and occupying a part of one surface 1A of the cell culture substrate 1, and a second segment PB disposed on the base 10 and occupying another part of the one surface 1A. The second segment PB is formed of a metal material and thus has a relatively higher surface free energy than the first segment PA formed of an inorganic material. The second segment PB is disposed such that a percentage R of an area $S_2$ of the second segment PB in a total area $S_{12}$ of the first segment PA and the second segment PB increases in a gradation direction (first direction) along the surface 1A.

Figure 3:
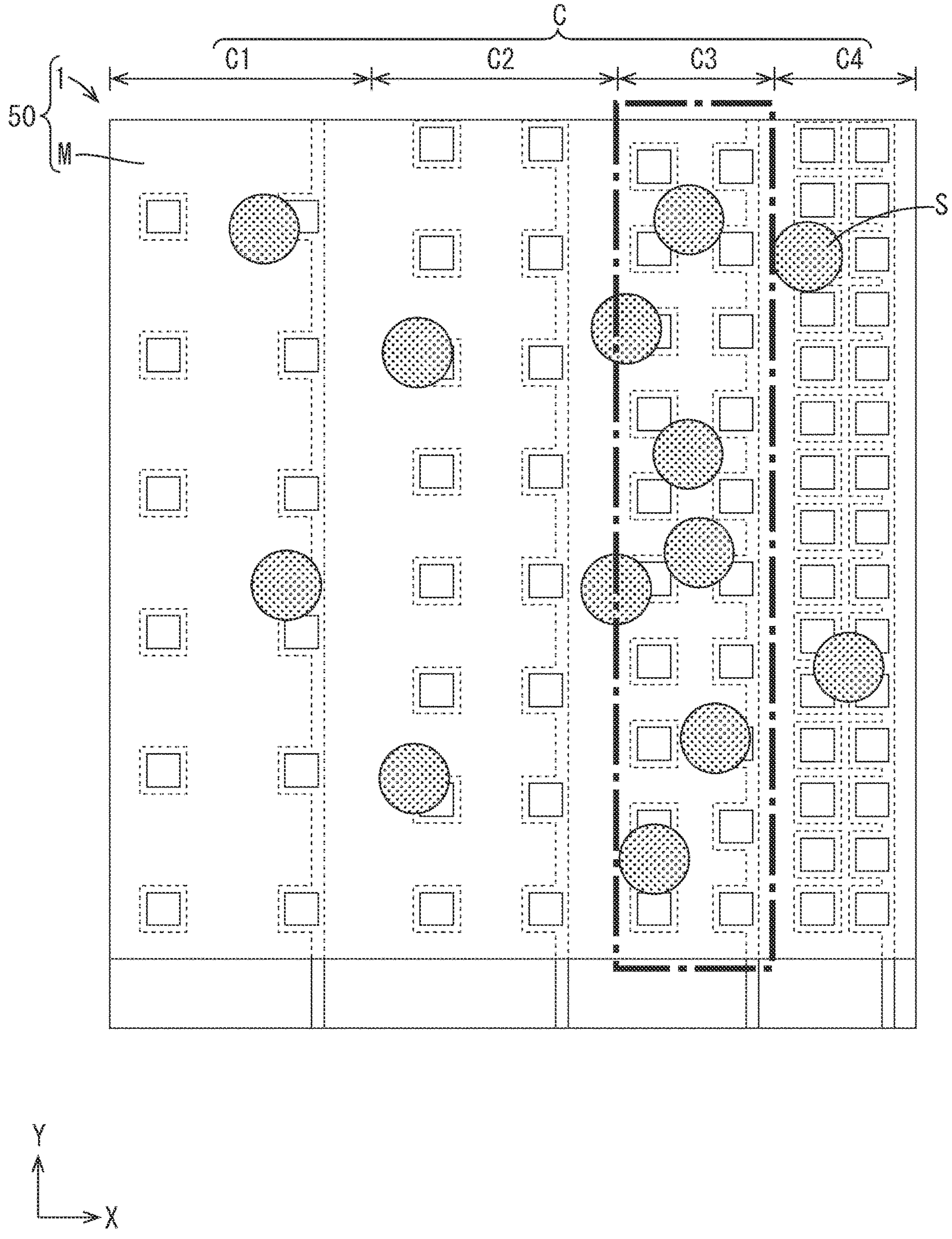
FIG. 3 is a schematic view showing how cells are cultured on a cell culture scaffold prepared using the cell culture substrate in FIG. 1.
Figure 6:
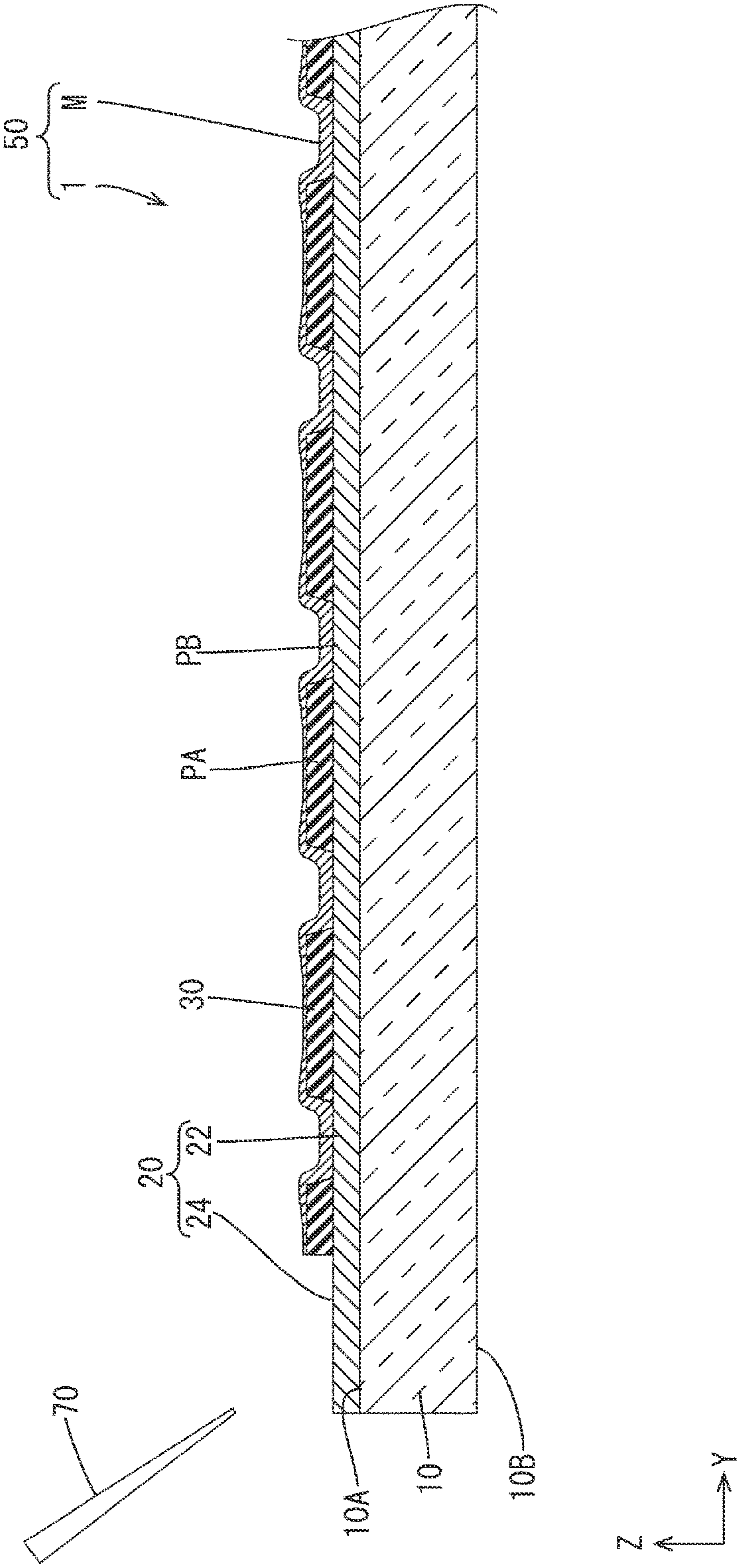
FIG. 6 is a sectional view corresponding to FIG. 3.

This cell culture substrate 1 is configured such that its hydrophilicity increases in the gradation direction. Therefore, when a coating solution M containing an extracellular matrix is supplied onto the surface of the cell culture substrate 1 to form an ECM coating layer, the coating solution M can be disposed in a larger amount on the second segment PB having a relatively higher surface free energy (higher hydrophilicity) than on the first segment PA, as shown in FIG. 6. As shown in FIG. 3, the distribution of the second segment PB is substantially the same in the cross direction but increases in the gradation direction. Accordingly, the concentration of the extracellular matrix is substantially the same in the cross direction but increases in the gradation direction. Thus, a cell culture scaffold 50 with varying extracellular matrix distribution concentrations can be prepared. By culturing a cell S using the cell culture scaffold 50, the cell S can grow preferentially in a region having an extracellular matrix concentration preferred by the cell S. For example, in the example of FIG. 3, the cell S prefers an extracellular matrix concentration in a culture region C3 among culture regions C1 to C4 and grows and divides promotedly in the culture region C3. In this manner, the cell culture scaffold 50 can provide the culture region C3 where the cell S can grow suitably. In the cell culture scaffold 50, the growth of the cell S is promoted, for example, along the cross direction. Thus, the direction of cell growth can be controlled in an environment where the cell S is free of stress.

The cell culture substrate 1 itself does not contain a biological material such as an extracellular matrix and thus is easy to store, and is useful in that a medium may be formed by supplying the coating solution M according to the timing of culture of the cell S. Therefore, according to the present technology, the cell culture substrate 1 and a reagent containing a coating agent can be combined and provided as a cell culture scaffold kit. The reagent may contain any coating agent for forming a medium disposed on the cell culture substrate 1. Examples of the coating agent contained in the reagent include proteins such as collagen, laminin, fibronectin, vitronectin, and gelatin, synthetic amino acids such as poly-D-lysine and poly-L-lysine, and artificially synthesized peptides. Any one of these may be contained, or two or more of these may be contained in combination. The reagent may be, for example, in liquid form, e.g., a concentrated solution or a diluted solution, or in lyophilized form with water removed.

In the above embodiment, the first segment PA is formed of an insulating inorganic material such as silicon nitride, silicon dioxide, or silicon oxynitride (at least one of an organic material containing no biological materials and an inorganic material). The second segment PB is formed of a metal material such as gold, titanium, or titanium nitride (at least one of a conductive inorganic material and a metal material). In general, the surface free energy of materials increases in the order of organic materials, inorganic materials, and metal materials. Therefore, when the first segment PA is formed of at least one of an organic material containing no biological materials and an inorganic material, and the second segment PB is formed of at least one of an inorganic material and a metal material, the surface 1A of the cell culture substrate 1 can be suitably constructed without using any biological materials. The second segment PB is desirably formed of an inorganic material because the cell culture substrate 1 can be provided with higher chemical stability.

In the above embodiment, the cell culture substrate 1 includes a conductive layer 20 covering a main surface 10A which is one surface of the base 10, and an insulating layer 30 covering the main surface 10A of the base 10 with the conductive layer 20 interposed therebetween. The insulating layer 30 constitutes the first segment PA and also has an opening 30A at a position corresponding to the second segment PB. The conductive layer 20 is exposed at the surface 1A through the opening 30A to constitute the second segment PB. In this configuration, when the cell S is cultured on the cell culture scaffold 50 prepared using the cell culture substrate 1, the second segment PB can come into contact with the cell S. As a result, the conductive layer 20 can send an action potential (electrical signal) emitted by the cell S from the second segment PB disposed in a region where the cell S grows to an external device through the wiring portion 24 (i.e., the action potential can be calculated). When an electrical signal is introduced into the wiring portion 24 using, for example, an electric probe 70, as shown in FIG. 6, the electrical signal passes through the conductive layer 20 (i.e., the wiring portion 24 and the electrode portion 22) and is applied to the cell S through the second segment PB. Thus, electrical stimulation can be applied to the cell at any desired timing. As a result, signal transfer from and to the cell can be performed. The first segment PA and the second segment PB having such a configuration are desirable because they can be formed with high accuracy as fine array patterns with different density distributions by using, for example, lithography technology.

In the above embodiment, the second segment PB is disposed such that the culture regions C1 to C4 (each being an example of a non-gradation region) in each of which the percentage of the area of the second segment PB is constant are formed along the cross direction intersecting the gradation direction (first direction). The conductive layer 20 includes a plurality of wiring portions 24 (examples of underlying wires) extending along the cross direction and spaced in the gradation direction. The plurality of wiring portions 24 are each disposed so as to connect with the plurality of second segments PB disposed in one of the culture regions C1 to C4.

According to the above configuration, the plurality of wiring portions 24 are each electrically connected to the plurality of second segments PB disposed in one of the culture regions C1 to C4 (non-gradation regions) in which the density distribution is constant. Therefore, when the cell S is cultured using the cell culture scaffold 50 prepared using the cell culture substrate 1, the cell S can grow in a growth direction controlled in a region having surface conditions preferred by the cell S (i.e., a region having an extracellular matrix concentration preferred by the cell), and the action potential of the cell S can be suitably measured. As a result, the growth and activity of the cell S can be investigated with reduced stress.

In the above embodiment, the base 10 is formed of a colorless transparent alkali-free glass plate (an example of a transparent material having insulating properties). This is suitable because the growth of the cell S can be observed through the back surface 10B opposite to the main surface 10A of the base 10, for example, when an inverted microscope or the like is used.

Second Embodiment

Figure 7:
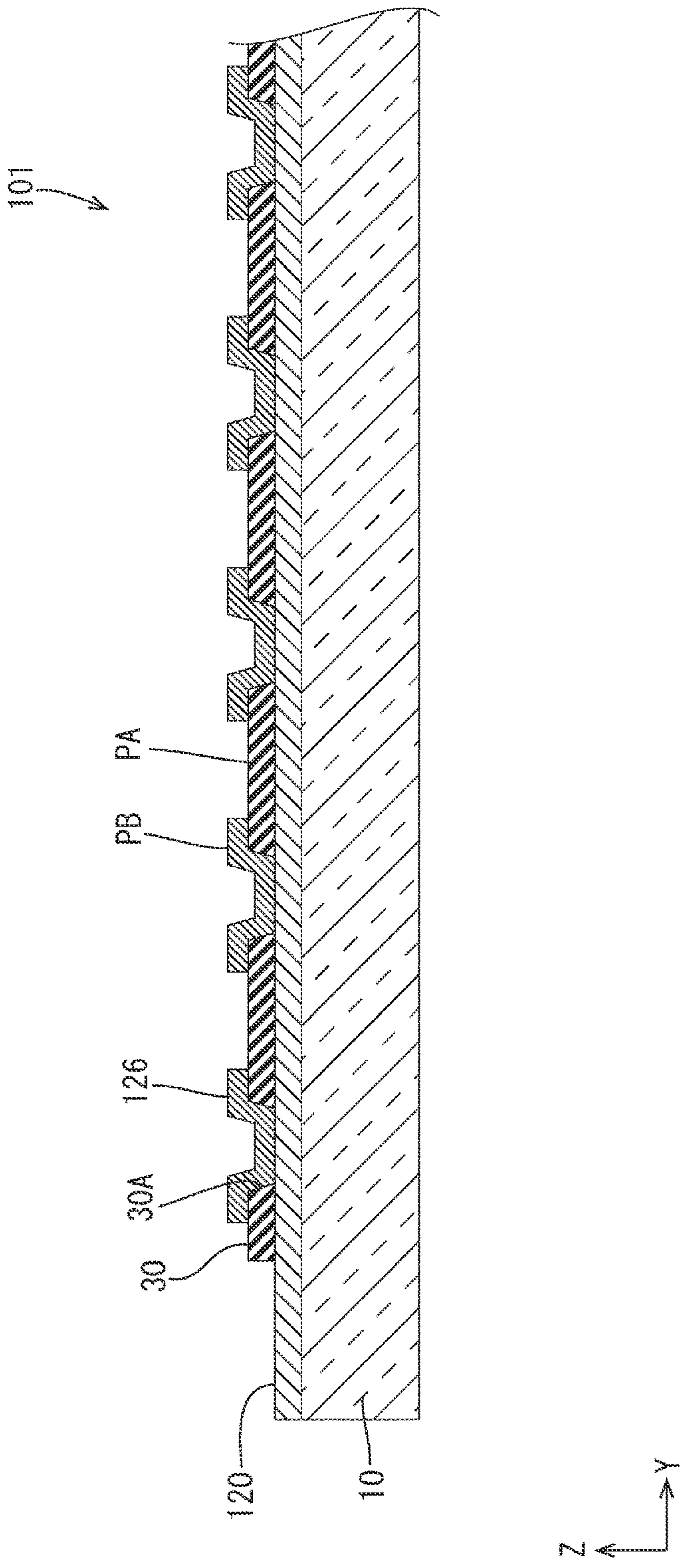
FIG. 7 is a sectional view of a cell culture substrate according to another embodiment.
Figure 8:
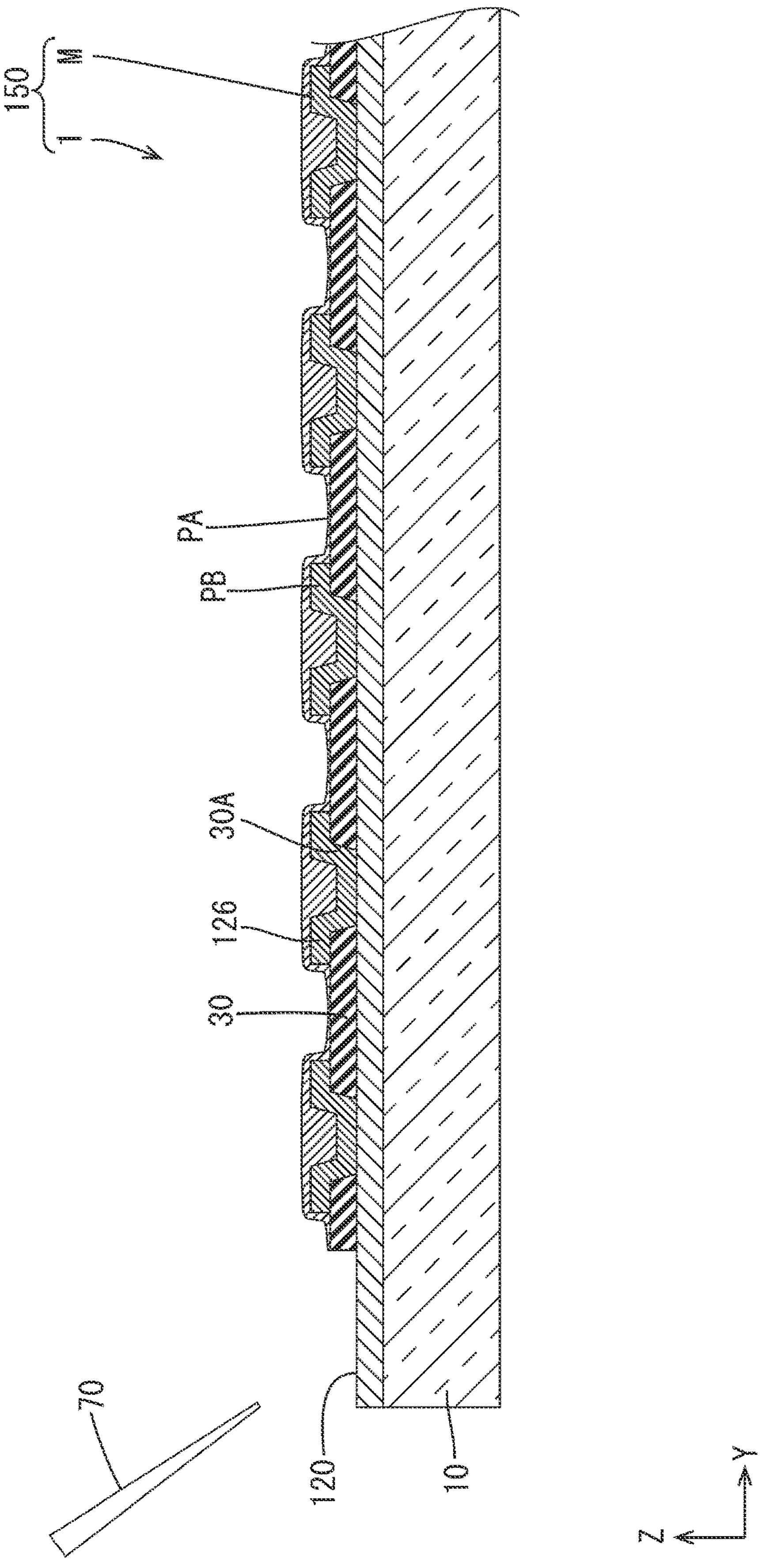
FIG. 8 is a sectional view of a cell culture scaffold prepared using the cell culture substrate in FIG. 7.

A cell culture substrate 101 according to a second embodiment will be described with reference to FIGS. 7 and 8. The cell culture substrate 101 according to the second embodiment includes a second conductive layer 126 and is different from the first embodiment in that the second segment PB is constituted not by a first conductive layer 120 but by the second conductive layer 126. The first conductive layer 120 is an element corresponding to the conductive layer 20 in the first embodiment. Since other configurations, and operations and effects are the same as those in the first embodiment, repetitive descriptions of the configurations, and operations and effects will be omitted.

The cell culture substrate 101 includes the second conductive layer 126 covering the opening 30A of the insulating layer 30. The second conductive layer 126 overlaps the insulating layer 30 at the peripheral edge of the opening 30A. The second conductive layer 126 is electrically connected to the first conductive layer 120 in the opening 30A. Thus, a surface of the cell culture substrate 101 includes the first segment PA constituted by the insulating layer 30 and the second segment PB constituted by the second conductive layer 126. According to this configuration, the first conductive layer 120 can be formed of a material having high electrical conductivity such as a metal material, and the second conductive layer 126 can be formed of a material (e.g., ITO) that has lower electrical conductivity but is less cytotoxic than metal materials. This allows a very small action potential from the cell S to be detected with higher accuracy. This can also reduce the deterioration of the second segment PB in a cell culture environment and the influence on the cell.

In addition, the second conductive layer 126 may be formed on the insulating layer 30 after the insulating layer 30 is formed. Therefore, the shape and size of the second segment PB can be easily and readily changed. For example, the second segment PB can be formed larger than the opening 30A, as shown in FIG. 8. Furthermore, the density distribution of the second segment PB can be easily and readily changed. The second conductive layer 126 is electrically connected to the first conductive layer 120 in the opening 30A and thus has a depressed surface. Therefore, a coating solution containing an extracellular matrix can be supplied in a larger amount into the depression. Furthermore, a cell culture scaffold 150 that has a steeper concentration distribution than the extracellular matrix can be prepared.

OTHER EMBODIMENTS

The technology disclosed herein is not limited to the embodiments described above with reference to the drawings. For example, embodiments as described below are also included in the technical scope.

(1) In the above embodiment, the base 10 is formed of a colorless transparent glass plate. However, the material of the base 10 is not limited to this example. For example, when a cell to be measured for its action potential is observed by the chemiluminescence or fluorescence method, the base may be formed of a white or black material.

Figure 9:
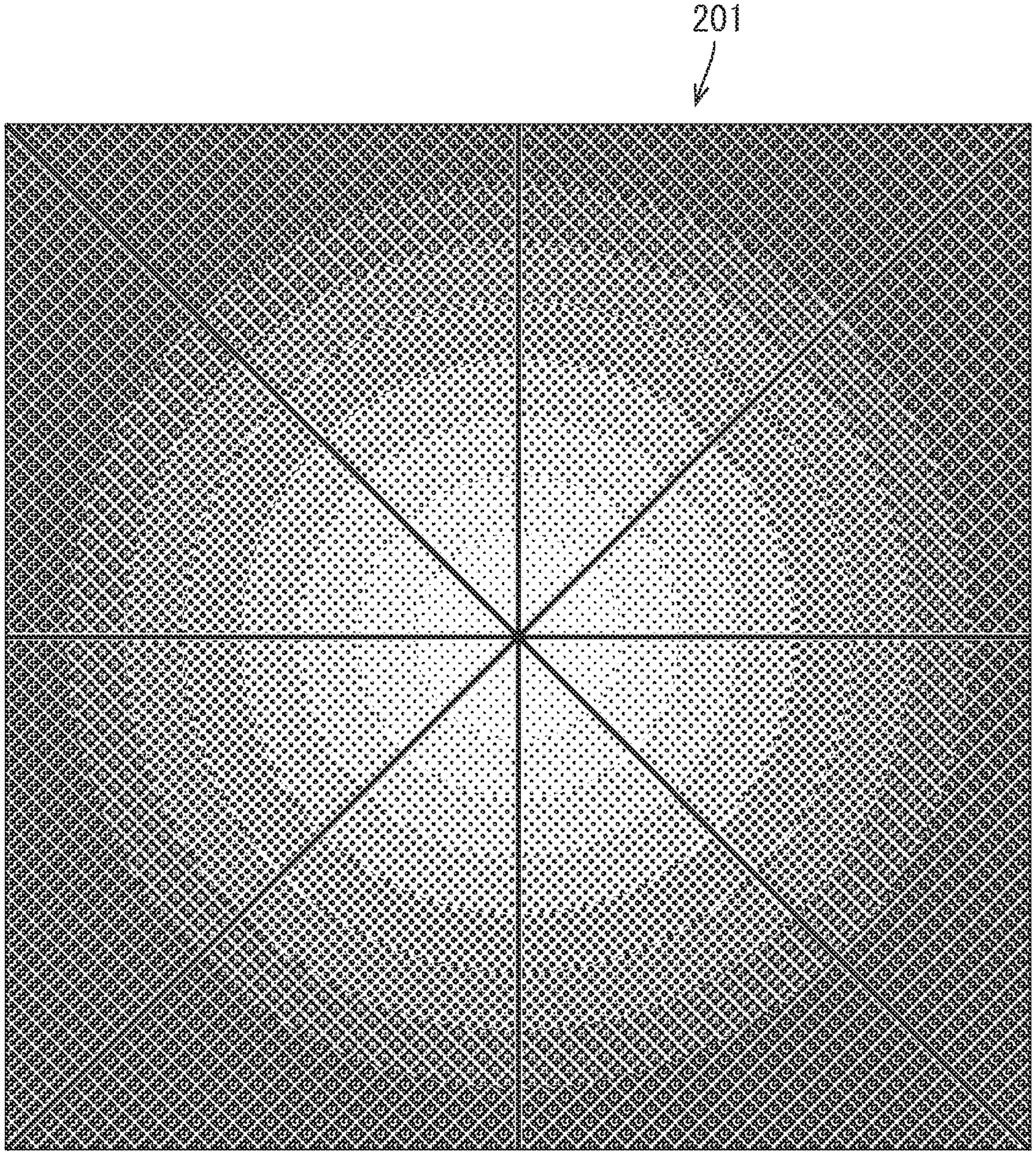
FIG. 9 is a plan view of a cell culture substrate according to another embodiment.
Figure 10:
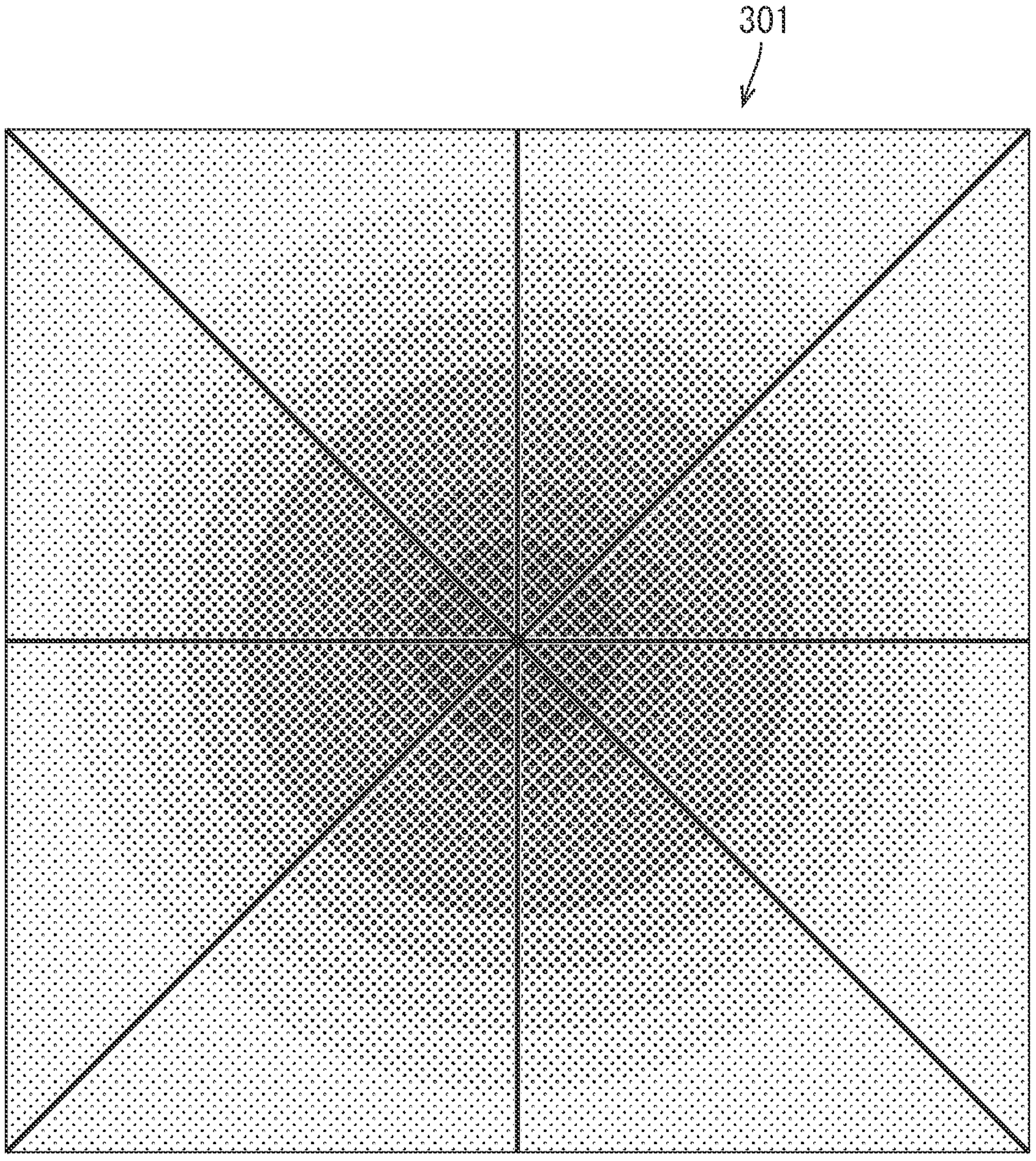
FIG. 10 is a plan view of a cell culture substrate according to another embodiment.

(2) In the above embodiment, the gradation direction (first direction) in which the percentage of the area of the second segment increases is only one direction. However, the gradation direction may be provided in two or more directions. For example, in a cell culture substrate 201 shown in FIG. 9, the gradation direction is provided radially outward from the center of the cell culture substrate. The cross direction is provided concentrically (in the circumferential direction) around the center of the cell culture substrate. Furthermore, in a cell culture substrate 301 shown in FIG. 10, the gradation direction is provided radially inward from the periphery to center of the cell culture substrate. The cross direction is provided concentrically (in the circumferential direction) around the center of the cell culture substrate. The gradation direction may be provided radially outward or inward not only in a circular shape but also in a polygonal shape. The gradation direction may be one direction along which a region where the percentage of the area of the second segment increases and then decreases and a region where the percentage of the area of the second segment decreases and then increases extends in any combination.

(3) In the above embodiment, the cell culture substrate is composed mainly of a base, a conductive layer, and an insulating layer. However, the cell culture substrate may additionally include a processor that processes a signal related to an action potential acquired via the conductive layer, a display that displays analysis results, and the like. The processor may be constituted by, for example, a microcomputer, and may be configured to execute an analysis program for analyzing signal data from an electrode, thereby, for example, in the case of nerve cells, performing a long-term measurement of action potentials to count neural activities (spikes), detect bursts, and, furthermore, analyze the network between the cells. In the case of muscle cells such as cardiac muscle, the processor may be configured to measure extracellular potentials and analyze response potential data regarding various reactions caused by contraction and relaxation of cardiac muscle.

The present disclosure contains subject matter related to that disclosed in Japanese Priority Patent Application JP 2022-046327 filed in the Japan Patent Office on Mar. 23, 2022, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A cell culture substrate used to prepare a cell culture scaffold, the cell culture substrate comprising:

a base;

a conductive layer; and an insulating layer, wherein:

the cell culture substrate has, in a plan view, a plurality of regions aligned along a first direction, the plurality of regions including a first region, a second region, and a third region sequentially arranged along the first direction, a surface of the cell culture substrate includes a first segment formed by the insulating layer, and a second segment formed by the conductive layer, the second segment has a relatively higher surface free energy than the first segment, a ratio of an area of the second segment to a particular area in the plan view is greater in the second region than in the first region, and greater in the third region than in the second region, and a ratio of an area of the first segment to the particular area in the plan view is smaller in the second region than in the first region, and smaller in the third region than in the second region.

2. The cell culture substrate according to claim 1, wherein the first segment is formed of at least one of an organic material containing no biological materials and a first inorganic material, and the second segment is formed of at least one of a second inorganic material and a metal material.

3. The cell culture substrate according to claim 1, wherein:

the conductive layer is a first conductive layer disposed on a main surface of the base, the insulating layer covers the main surface of the base with the first conductive layer interposed between the insulating layer and the main surface, and has a plurality of openings exposing the first conductive layer, and portions of the first conductive layer overlapping the plurality of openings are exposed by the plurality of openings to form the second segment.

4. The cell culture substrate according to claim 3, wherein the first conductive layer includes a plurality of electrode portions respectively disposed corresponding to the plurality of openings, and a plurality of underlying wires each extending along a cross direction intersecting the first direction and spaced in the first direction, and each of the plurality of underlying wires is disposed in one region of the plurality of regions and is connected to two or more electrode portions disposed in the one region of the plurality of regions.

5. The cell culture substrate according to claim 3, wherein the plurality of openings include a plurality of first openings disposed in the first region and aligned along a cross direction intersecting the first direction, a plurality of second openings disposed in the second region and aligned along the cross direction, and a plurality of third openings disposed in the third region and aligned along the cross direction, and a number of the plurality of second openings is greater than a number of the plurality of first openings, and a number of the plurality of third openings is greater than the number of the plurality of second openings.

6. The cell culture substrate according to claim 3, wherein the plurality of openings include a plurality of first openings disposed in the first region and aligned at regular intervals along a cross direction intersecting the first direction, a plurality of second openings disposed in the second region and aligned at regular intervals along the cross direction, and a plurality of third openings disposed in the third region and aligned at regular intervals along the cross direction, and a regular interval of the plurality of second openings is smaller than a regular interval of the plurality of first openings, and a regular interval of the plurality of third openings is smaller than the regular interval of the plurality of second openings.

7. The cell culture substrate according to claim 1, further comprising:

a first conductive layer disposed on a main surface of the base;

and a plurality of second conductive layers, each covering a corresponding opening of the plurality of openings, and connected to the first conductive layer in the corresponding opening, wherein:

the insulating layer covers the main surface of the base with the first conductive layer interposed between the insulating layer and the main surface, and has a plurality of openings exposing the first conductive layer, a portion of the insulating layer not overlapping the plurality of second conductive layers forms the first segment, and the plurality of second conductive layers forms the conductive layer, and forms the second segment.

8. The cell culture substrate according to claim 7, wherein the first conductive layer includes a plurality of electrode portions respectively disposed corresponding to the plurality of openings, and a plurality of underlying wires, each extending along a cross direction intersecting the first direction and spaced in the first direction, and each of the plurality of underlying wires is disposed in one region of the plurality of regions and is connected to two or more electrode portions disposed in the one region of the plurality of regions.

9. The cell culture substrate according to claim 7, wherein the plurality of openings include a plurality of first openings disposed in the first region and aligned along a cross direction intersecting the first direction, a plurality of second openings disposed in the second region and aligned along the cross direction, and a plurality of third openings disposed in the third region and aligned along the cross direction, and a number of the plurality of second openings is greater than a number of the plurality of first openings, and a number of the plurality of third openings is greater than the number of the plurality of second openings.

10. The cell culture substrate according to claim 7, wherein the plurality of openings include a plurality of first openings disposed in the first region and aligned at regular intervals along a cross direction intersecting the first direction, a plurality of second openings disposed in the second region and aligned at regular intervals along the cross direction, and a plurality of third openings disposed in the third region and aligned at regular intervals along the cross direction, and a regular interval of the plurality of second openings is smaller than a regular interval of the plurality of first openings, and a regular interval of the plurality of third openings is smaller than the regular interval of the plurality of second openings.

11. The cell culture substrate according to claim 1, wherein the second segment has a contact angle with water of 45° or less.

12. The cell culture substrate according to claim 1, wherein the second segment has a surface on which a hydrophilic functional group is introduced.

13. The cell culture substrate according to claim 1, wherein a minimum circumscribed circle of the second segment has a radius of 2 μm or more and 100 μm or less.

14. The cell culture substrate according to claim 1, wherein the base is formed of a transparent material having insulating properties.

15. A cell culture scaffold kit comprising:

the cell culture substrate according to claim 1; and a reagent containing a coating agent for forming a medium to be disposed on the cell culture substrate.

16. The cell culture substrate according to claim 1, wherein each of the plurality of regions has a length in a direction orthogonal to the first direction that is longer than a length in the first direction.

* * * * *